United States Patent [19]

Bramanti et al.

[11] Patent Number: 4,754,214

[45] Date of Patent: Jun. 28, 1988

[54] METHOD AND APPARATUS FOR DETERMINING THE DIELECTRIC CONSTANT OF MATERIALS, IN PARTICULAR HEATER ASH

[75] Inventors: Mauro Bramanti, Lucca; Andrea Del Bravo, Pisa, both of Italy

[73] Assignees: Consiglio Nazionale Delle Ricerche; Enel - Ente Nazionale per l'Energia Elettrica, both of Rome, Italy

[21] Appl. No.: 928,351

[22] Filed: Nov. 10, 1986

[30] Foreign Application Priority Data

Nov. 8, 1985 [IT] Italy ................................ 9515 A/85

[51] Int. Cl.[4] ............................................ G01R 27/06
[52] U.S. Cl. ............................. 324/58 B; 324/58.5 R
[58] Field of Search ..................... 324/58 B, 58.5 R; 266/80

[56] References Cited

U.S. PATENT DOCUMENTS

| 3,025,463 | 3/1962 | Luoma et al. | 324/58.5 B |
| 3,701,943 | 10/1972 | Kaiser | 324/58.5 R |
| 4,104,584 | 8/1978 | Miyai et al. | 324/58.5 R |
| 4,345,202 | 8/1982 | Nagy et al. | 324/58.5 B |

FOREIGN PATENT DOCUMENTS

| 69969 | 1/1983 | European Pat. Off. |
| 3317215 | 11/1983 | Fed. Rep. of Germany |
| 2560998 | 9/1985 | France |

OTHER PUBLICATIONS

Bahl, et al., "Analysis of a Microstrip Covered with a Lossy Dielectric", *IEEE Trans. Microwave Theory and Tech.*, vol. MTT 28, No. 2, pp. 104–109, Feb. 1980.

Hitchin et al., "Rapid Method Suitable for Liquids and Powders for Determination of Relative Permittivities in the Microwave Region", *Electronics Letters*, vol. 9, No. 2, 1/25/73, pp. 39–40.

Everett et al., "A Computer-Controlled Dielectric Constant Measurement System: The Moving Vane Dielectometer", 1982 IEEE MTT-S International Microwave Symposium Digest, Dallas, Tex., 15th–17th Jun. 1982, pp. 325–327.

Musil et al., "New Microwave System to Determine the Complex Permittivity of Small Dielectric and Semiconducting Samples", 10th–13th Sept. 1974, pp. 66–70.

*Primary Examiner*—A. D. Pellinen
*Assistant Examiner*—Morris Ginsburg
*Attorney, Agent, or Firm*—Browdy and Neimark

[57] ABSTRACT

A method and an apparatus for determining the dielectric constant of a material wherein the material is loaded to a short-circuited microstrip and microwaves are fed to the microstrip for providing a reflected signal. The reflected signal is compared with a reference signal both under load and not load conditions of the microstrip for obtaining the modulus and the phase of the reflection coefficient, the dielectric constant being a function thereof. The measure of the phase angle between the reference and the reflected signal in both conditions is obtained by handling the reflected signal with a first phase shifter and a second calibrated phase shifter cooperating with a zero detector. The method and the apparatus of the invention is especially designed for a quick and easy measure of the amount of unburnt coal in the ash coming from a combustion heater.

7 Claims, 1 Drawing Sheet

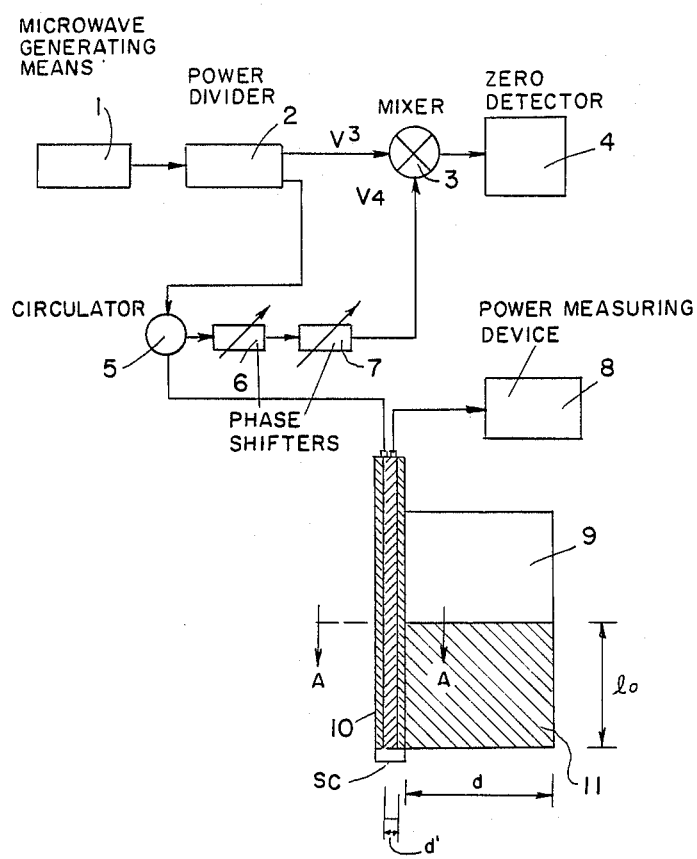
FIG. 1
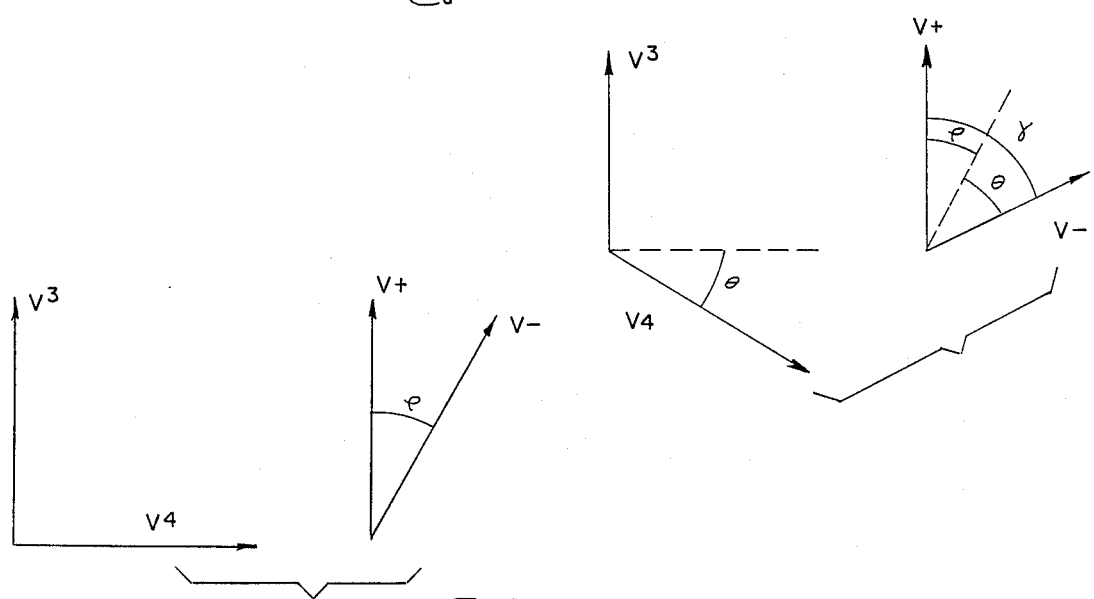
FIG. 3
FIG. 2

METHOD AND APPARATUS FOR DETERMINING THE DIELECTRIC CONSTANT OF MATERIALS, IN PARTICULAR HEATER ASH

FIELD OF THE INVENTION

The present invention relates to a method and an apparatus for determining the dielectric constant of a material, said dielectric constant being important, inter alia, for determining the unburnt coal content in the ash coming from a heater of any kind. Such a measure is particularly useful when testing heaters whose structure is still under experimental condition, because it is obviously correlated to the heater efficiency.

BACKGROUND OF THE INVENTION

The only known method for measuring the content of unburnt coal in the ash is to perform a chemical analysis of the ash itself. This method is often unsuitable because in most cases the parameter would have to be known in real time, that is as the ash is being formed. On the other side, very often, the knowledge of said parameter is not requested with an high degree of accuracy as attainable through the chemical analysis methods.

Anyway, it is known that the dielectric constant of a dielectric material is a function of the content of conductive particles in the material: the higher the conductive particles concentration, the higher will be the dielectric constant of the material, both as far as its real part and imaginary part are concerned.

In particular the coal ash without unburnt coal has the characteristic of a substantially perfect dielectric material, i.e. with a very low value of the imaginary part of the dielectric constant.

On the contrary, unburnt coal has a conductivity substantially other than zero. Therefore, the presence of more unburnt coal in the ash increases the dielectric constant, and the unburnt concentration is greater. The increase affects both the real part and the imaginary part of the dielectric constant; thus, in order to have a thorough evaluation of the phenomenon, in the following reference will be made to the modulus of the dielectric constant, except when specified to the contrary.

The present technical knowledge teach that a bi-univocal correspondence exists between the concentration of unburnt coal in the ash and the dielectric constant of the ash itself. The theoretical study of the problem with the purpose of making analytically explicit such a biunivocal correspondance, is not necessary. What is necessary is only a calibration curve which can be easily obtained from several samples of ash characterized by known unburnt concentrations measured, for example, by chemical analysis.

The calibration curve being known, the technical problem is therefore how to measure the ash dielectric constant in a quick and easy way. Unfortunately the methods and apparatuses that have been proposed up to now, involve the use of samples of well defined shape and also are unsuitable for characterizing materials having comparatively high losses.

SUMMARY OF THE INVENTION

The object of the present invention is to provide an apparatus and a method for the measure of the dielectric constant of a material, in particular ash from a combustion heater, capable of being actuated without requesting the shaping of the material to be tested according to shapes which are difficult to make.

It is another object of the present invention to provide an apparatus which is above mentioned type of the low cost and easy to operate without any special training.

According to the invention, there is provided an apparatus for determining the dielectric constant of a material, comprising: a short circuited microstrip and container means associated therewith for maintaining said material in contact with said microstrip; microwave generating means for feeding microwaves to said microstrip and providing a reference signal; means for detecting the phase displacement between a signal reflected by said microstrip and said reference signal; power measuring means applied to said microstrip for providing the modulus of the reflection coefficient; first and second control means for varying said phase displacement by varying the phase between said reference signal and said reflected signal, said control means for measuring the phase displacement between said signals, whereby the phase of the reflection coefficient can be obtained as a function of said measure, said phase being correlated to the value of the dielectric constant.

According to the invention there is further provided a method for determining the dielectric constant of a material, said method comprising the steps of: numerically making the function between the complex reflection coefficient and the dielectric constant explicit; obtaining the modulus of said reflection coefficient from a measure of the microstrip output power; obtaining the phase of said reflection coefficient by operating a calibrated phase shifter.

BRIEF DESCRIPTION OF THE DRAWINGS

One way of carrying out the invention is described in detail below with reference to drawings which illustrate only one specific embodiment, in which:

FIG. 1 is a schematic diagram of the apparatus according to the invention;

FIG. 2 shows the phase ratio of the signals $V_3$ and $V_4$ shown in FIG. 1 and, respectively, of the signals $V+$ and $V-$ detectable in the microstrip, in correspondance of the section A—A of FIG. 1, when the microstrip is unloaded; and FIG. 3 shown the same signals of FIG. 2 when the microstrip is loaded.

DETAILED DESCRIPTION OF THE PREFERRED EMBODIMENT

For a better understanding of the operating principle of the apparatus according to the present invention, it is necessary to set out some elements about the microstrips for transmission of high frequency signals.

A microstrip is a strip of conductive material of width W separated by a conductive plane of width approximately ten times greater than W by means of a substrate of dielectric constant $\epsilon_1$ and thickness $d'$.

Since the substrate is constituted by a perfect dielectric material, its dielectric constant is real. When a sample of dielectric material of height d, width equal (or greater) than that of the conductive plane and dielectric constant $\epsilon_2$ is placed on the microstrip, the latter is said to be "loaded". As the loading material generally has a conductivity other than zero, this would be generally complex. It can be demonstrated that the characteristic impedance of the loaded microstrip is given by $$Z_o = \frac{1}{c\pi\epsilon_o} \sqrt{I I_o} \qquad (1)$$

where:
c = free space light velocity
$\epsilon_0$ = vacuum dielectric constant.

$$I = \int_0^1 \frac{\left\{1{,}6\frac{\sin\left(\frac{1-x}{x}\right)}{\frac{1-x}{x}} + \frac{2{,}4}{\left(\frac{1-x}{x}\right)^2}\left[\cos\left(\frac{1-x}{x}\right) - 2\frac{\sin\left(\frac{1-x}{x}\right)}{\frac{1-x}{x}} + \frac{\sin^2\left(\frac{1-x}{x}\right)}{\left(\frac{1-x}{x}\right)^2}\right]\right\}^2}{\left[\epsilon_2\frac{\epsilon_2 \, tgh\left(\frac{2d}{w}\frac{1-x}{x}\right)+1}{\epsilon_2 + tgh\left(\frac{2d}{w}\frac{1-x}{x}\right)} + \frac{\epsilon_1}{tgh\left(\frac{2d'}{w}\frac{1-x}{x}\right)}\right] \times (1-x)} dx \qquad (2)$$

and $$I_o = I \text{ when } \epsilon_2 = \epsilon_1 = 1 \qquad (3)$$

It has to be pointed out that generally I is complex if $\epsilon_2$ is complex; on the contrary, $I_0$ is always real.

Referring now to the FIG. 1, a microstrip 10 has been short-circuited and loaded with a material placed in a container 9 for a length $l_0$. The material 11 has a characteristic dielectric constant $\epsilon_2$. In this case the input impedance for the section A—A of FIG. 1 is given by:

$$Z_{in} = jZ_o \cdot tg\beta \cdot l_o \qquad (4)$$

where $Z_o$ is the characteristic impedance of the loaded microstrip and $$\beta = \frac{2}{\lambda} \sqrt{\epsilon e} \qquad (5)$$

$\lambda$ being the wave length in the free space and $$\epsilon e = \frac{I_o}{I} \qquad (6)$$

As is known, the reflection coefficient $\Gamma$ for the section A—A is given by $$\Gamma = \frac{Z_{in} - Z_A}{Z_{in} + Z_A} \qquad (7)$$

where $Z_A$ is the characteristic impedance of the not loaded microstrip.

Putting $$\rho = \frac{1}{v/2} \qquad (8)$$

we obtain $$\Gamma = \frac{-Z_A + j\frac{\sqrt{I I_o}}{c\pi\epsilon_o} tg\left[\pi\rho\sqrt{\frac{I_o}{I}}\right]}{Z_A + j\frac{\sqrt{I I_o}}{c\pi\epsilon_o} tg\left[\pi\rho\sqrt{\frac{I_o}{I}}\right]} \qquad (9)$$

This equation shows that the reflection coefficient $\Gamma$, beside depending on the dielectric constant $\epsilon_2$ of the loading material, also depends, through I and $I_0$, on the following parameters:
w = linear length of the microstrip,
d' = substrate height,
$\epsilon_1$ = substrate dielectric constant,
d = height of the loading material.

The first three parameter depend on the type of microstrip used and therefore are known; the fourth parameter depends on the height of the sample placed on the microstrip.

It can be easily understood that, if the height d of the sample is greater than a certain minimum value, the reflection coefficient $\Gamma$ no longer depends on said parameter; in order to let the reflection coefficient become independent from this parameter, it is sufficient to use material samples of height greater than a minimum d value.

For instance, using a microstrip of the type known as POLIGUIDE having a vacuum characteristic impedance of 50Ω, the physical parameters of the microstrip are the following:
d' = 1.6 mm
w = 4.8 mm
$\epsilon_1$ = 2.32

As regards the fourth parameter, it has been found for d a minimum value of $d_1 = 7.5$ cm approximately.

The last parameter affecting the reflection coefficient $\Gamma$ is $l_0$ and this parameter can be directly measured once for all measurements. Thus, as can be seen in FIG. 1, to the microstrip 10 there has been fixed a suitable container 9 made of plexiglass where the material to be tested has been placed for a length equal to $l_0$.

Microwave generating means 1 supplies microwaves to a power divider 2 whose output is constituted by two perfectly in phase signals. The first signal is directly sent to a mixer 3 and this signal will be indicated at $V_3$ in the following description. The second signal is sent to a circulator 5 by which it is sent to the microstrip 10, which, being shortcircuited, sends it back to the circulator 5. Furthermore circulator 5 sends the signal back to mixer 3 via phase shifters 6 and 7 ($V_4$). The mixer output is fed to a zero detector 4, in the present case a voltmeter. A power measuring device 8, in the present case a wattmeter, is also associated with microstrip 10.

The measure of the modulus of the reflection coefficient is immediate, being sufficient to measure the output power from the microstrip 10 by means of wattmeter 8 in both cases, i.e. when the microstrip is loaded (power value equal to $P_2$) and when the microstrip is not loaded ($P_1$). The modulus of the reflection coefficient is given by:

$$|\underline{\Gamma}| = \sqrt{\frac{P_2}{P_1}} \qquad (10)$$

From the foregoing it is understood that it is now required to only measure the phase of the reflection coefficient in the section A—A of FIG. 1.

Indicating at $V^+$ the signal, i.e. the wave, entering the microstrip in correspondence to the section A—A and at $V^-$ the signal, i.e. the wave, coming back from the same section, the phase of the reflection coefficient is the phase angle between the two signals, i.e.

$$<\underline{\Gamma} = <\frac{V^-}{V^+} \qquad (11)$$

It has to be considered that mixer 3 provides an output voltage equal to zero when the signals $V_3$ and $V_4$ at its input ends are in quadrature, i.e. shifted 90° out of phase. Therefore, it is easy to control when these signals are shifted 90° out of phase by means of the zero measurer 4 and the line delay can be varied by operating the not calibrated phase shifter 6. Assuming the microstrip not loaded at the beginning and putting the signals $V_3$ and $V_4$ in quadrature by controlling this operation with the zero detector 4, the signal situation is that graphically illustrated in FIG. 2 by means of the phase diagrams. The angle $\phi$ is the phase of the reflection coefficient of the not loaded microstrip and can be easily calculated theoretically. In fact, this angle is given by:

$$\phi = \pi - 2\beta l_o \qquad (12)$$

where $$\beta = \frac{2\pi}{\lambda} \sqrt{\epsilon e} \qquad (13)$$

and $$\epsilon e = \frac{I_o}{I} \qquad (14)$$

I being the integral (2) when the loaded material is air, i.e. the microstrip is not loaded. Putting again $\rho = l_o/\lambda/2$ and substituting in (12), it is obtained $$\phi = \pi - 2\pi\rho \cdot \sqrt{\frac{I_o}{I}} \qquad (15)$$

With the previously defined values of the various parameters, it is:
$I_0 = 0.594311$
$I = 0.302328$ If now the microstrip is loaded, as schematically shown in FIG. 1, with a sample of length $l_0$, the signal $V^-$ will be further delayed with respect to the signal $V^+$ of an angle $\theta$ and the same angle will be delayed $V_4$ with respect to $V_3$.

The actual phase situation is visualized in FIG. 3 and the angle $$\gamma = \phi + \theta$$

is the phase of the reflection coefficient in correspondance of the section A—A of the loaded microstrip. The angle $\phi$ being known, the angle $\theta$ remains to be determined. Due to the delay of $V_4$ with respect to $V_3$, the output of mixer 3 is now unbalanced. This is visualised by the zero detector 4. The measure of the angle $\theta$ is performed by means of a calibration phase shifter 7. In fact, if by means of the latter the output of mixer 3 is set to zero again, this means that phasor $V_4$ will be in advance just of the angle $\theta$. Therefore this parameter can be directly read from the calibrated phase shifter 7. It has to be pointed out that the zero setting does not depend on possible amplitude variations of the signal $V_4$. The apparatus schematically shown in FIG. 1 obviously operates in the field of the microwaves, i.e. having a frequency greater than 1 GHz. The selection of the proper frequency value is anyway affected by the following considerations:

the frequency value must be consistent with the use of microstrip type transmission lines;

it is advisable that the value be in a range where compact and easy to be found electronic components are available;

this value must be so that $$\rho = \frac{2 l_o}{\lambda} < 0.8$$

in order to avoid any ambiguity about the determination of the angle $\theta$. An optimum value balancing the various requirements is about 2 GHz.

In the particular case where the tested material is ash coming from a combustion heater, having determined the phase and the modulus of the reflection coefficient, it is possible to calculate the dielectric constant and then, by means of the previously prepared calibration curve, obtain the amount of unburnt coal present in the ash.

As can be appreciated, according to the invention the value of the dielectric constant is obtained by means of a low cost apparatus, that does not request the use of samples of particular shape or amount. Furthermore the initial zero setting in the absence of the material to be tested, makes the measure unaffected by any deviation of the real apparatus from what assumed by the theory.

We claim:

1. Apparatus for determining the content of unburnt coal in an ash coming from a combustion heater, said content being a function of the dielectric constant of the ash, comprising:

a short-circuited microstrip and container means associated therewith for maintaining the ash in contact with said microstrip;

microwave generating means for feeding microwaves to said microstrip and providing a reference signal;

means for detecting a phase displacement between said reference signal and a signal reflected by said microstrip;

power measuring means applied to said microstrip for providing the modulus of the reflection coefficient;

control means for varying said phase displacement by varying the phase between said reference signal and said reflected signal, said control means measuring the phase displacement between said signals, whereby the value of the dielectric constant is obtained from the modulus of the reflection coefficient and the phase thereof which is a function of said phase displacement measure.

2. Apparatus according to claim 1, wherein said container means has a side perpendicular to said microstrip, the length of said side being greater than a value $d_1$, said value $d_1$ being a function of said material and said microstrip.

3. Apparatus according to claim 2, wherein said means for detecting the phase displacement between the reference and the reflected signals comprises a mixer having said reference and reflected signals as inputs and a voltage signal equal to zero as an output when said signals are in quadrature, and a voltmeter for detecting said voltage signal.

4. Apparatus according to claim 3 wherein said control means comprises a first phase shifter for 90° phase displacing the signal reflected by the microstrip, under no-load condition, with respect to said reference signal and a second calibrated phase shifter for 90° phase displacing the signal reflected by the microstrip, under load condition, with respect to said reference signal.

5. Apparatus according to claim 1, further comprising means for calculating the dielectric constant from the reflection coefficient and the content of unburnt coal from the dielectric constant.

6. A method for determining the content of unburnt coal in an ash coming from a combustion heater, comprising the steps of:
loading a short-circuited microstrip associated with microwave generating means for providing a reference signal and for feeding said microstrip with microwaves so that a reflected signal is generated therefrom,
making the function between the reflection coefficient $\underline{\Gamma}$ of said reflected signal and the dielectric constant numerically explicit;
obtaining the modulus of said reflection coefficient by measuring output power from the microstrip, respectively when said microstrip is loaded with the ash and when it is not loaded, said modulus being given by $$|\underline{\Gamma}| = \sqrt{\frac{P \text{ loaded}}{P \text{ not loaded}}} \; ; \text{ and}$$

measuring the phase of said reflection coefficient.

7. Method according to the claim 6, wherein the step of measuring the phase of said reflection coefficient comprises the steps of:
feeding the same signal to a first circuit for providing said reference signal and to a second circuit comprising said microstrip and a first phase shifter and a second calibrated phase shifter
adjusting the phase difference between said referece and reflected signals by means of said first phase shifter so as to make said difference equal to 90° when the microstrip is not loaded;
measuring the phase angle of the reflection coefficient when the microstrip is not loaded;
loading said microstrip with the ash;
adjusting the phase difference between said reference and reflected signals by means of said second calibrated phase shifter, so as to make said difference equal to 90° again, and reading the relative phase displacement $\theta$ from said second calibrated phase shifter, whereby the total phase displacement can be obtained from $\gamma = \theta + \phi$, the angle $\gamma$ being the phase of the reflection coefficient.

* * * * *